United States Patent
Nakagawa

(10) Patent No.: US 11,657,343 B2
(45) Date of Patent: May 23, 2023

(54) METHODS AND SYSTEMS FOR IDENTIFYING SERVICE PROVIDERS AND PROVIDING SERVICES

(71) Applicant: TOYOTA MOTOR NORTH AMERICA, INC., Plano, TX (US)

(72) Inventor: Masashi Nakagawa, Sunnyvale, CA (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 0 days.

(21) Appl. No.: 17/218,499

(22) Filed: Mar. 31, 2021

(65) Prior Publication Data
US 2022/0318717 A1 Oct. 6, 2022

(51) Int. Cl.
*G06Q 10/0631* (2023.01)
*G16H 40/20* (2018.01)
(Continued)

(52) U.S. Cl.
CPC ........... *G06Q 10/063112* (2013.01); *G06Q 10/063118* (2013.01); *G06Q 10/20* (2013.01);
(Continued)

(58) Field of Classification Search
CPC combination set(s) only.
See application file for complete search history.

(56) References Cited

U.S. PATENT DOCUMENTS 8,943,187 B1 * 1/2015 Saylor .............. H04L 67/306
709/225
10,360,744 B1 * 7/2019 Kerzner ............ H04N 7/181
(Continued)

FOREIGN PATENT DOCUMENTS

KR 20010008205 A 2/2001
WO WO-2016010649 A1 * 1/2016 ............ G06Q 50/00

OTHER PUBLICATIONS

M. A. Hossain et al., "A Technology Assisted Framework for Medical Emergencies Involving Formal and Informal Caregivers," 2018 IEEE Intl Conf on Parallel & Distributed Processing (ISPA/IUCC/BDCloud/SocialCom/SustainCom), 2018, pp. 1064-1070, doi: 10.1109/BDCloud.2018.00159. (Year: 2018).*
(Continued)

*Primary Examiner* — Crystol Stewart
(74) *Attorney, Agent, or Firm* — Dinsmore & Shohl LLP

(57) ABSTRACT

A method and system for identifying and providing access to a user capable of performing medical services. The method includes receiving a message from a first device of a first user, the message including a request and digital authorization data associated with the first user, identifying, within a proximity of a first location of the first device, a second device of a second user capable of performing an action associated with the request, determining whether the second user provided agreement to perform the action, communicating the digital authorization data to the second device of the second user responsive to determining that the second user provided the agreement, and instructing, responsive to determining that the second user provided the agreement, a vehicle to transport the second user from a second location of the second device to the first location.

14 Claims, 5 Drawing Sheets

(51) Int. Cl.
*H04W 4/40* (2018.01)
*G06Q 10/20* (2023.01)
*G06Q 50/30* (2012.01)
*H04W 4/02* (2018.01)
*H04W 4/021* (2018.01)
*B60W 60/00* (2020.01)
*B60P 3/14* (2006.01)
*G05D 1/02* (2020.01)

(52) U.S. Cl.
CPC ............ *G06Q 50/30* (2013.01); *G16H 40/20* (2018.01); *H04W 4/02* (2013.01); *H04W 4/021* (2013.01); *H04W 4/40* (2018.02); *B60P 3/14* (2013.01); *B60W 60/00253* (2020.02); *G05D 1/0212* (2013.01); *G06Q 2240/00* (2013.01)

(56) References Cited

U.S. PATENT DOCUMENTS

| | | | |
|---|---|---|---|
| 10,721,274 B1* | 7/2020 | Prasad | H04W 4/38 |
| 10,834,523 B1* | 11/2020 | Rao | H04W 4/021 |
| 11,222,299 B1* | 1/2022 | Baalke | G06Q 10/087 |
| 2006/0010019 A1* | 1/2006 | Phillips | G06Q 30/02 705/7.29 |
| 2007/0250342 A1 | 10/2007 | Sohal | |
| 2009/0112623 A1 | 4/2009 | Schoenberg | |
| 2009/0204457 A1* | 8/2009 | Buhrmann | G06Q 40/02 455/410 |
| 2010/0077349 A1 | 3/2010 | Neal | |
| 2012/0109747 A1 | 5/2012 | Bircoll | |
| 2014/0278450 A1 | 9/2014 | Schoenberg | |
| 2016/0371620 A1* | 12/2016 | Nascenzi | G06Q 10/06314 |
| 2017/0316629 A1* | 11/2017 | López Miranda | G06Q 10/02 |
| 2018/0060778 A1 | 3/2018 | Guo et al. | |
| 2018/0126952 A1* | 5/2018 | Niemiec | G07C 9/20 |
| 2018/0240545 A1* | 8/2018 | Brown | G16H 80/00 |
| 2018/0322775 A1* | 11/2018 | Chase | G06Q 10/02 |
| 2018/0342329 A1* | 11/2018 | Rufo | G08B 25/10 |
| 2019/0043104 A1* | 2/2019 | Bonnet | G06Q 20/405 |
| 2019/0095871 A1* | 3/2019 | Abney | G06Q 30/0621 |
| 2019/0122760 A1* | 4/2019 | Wang | G06Q 10/1093 |
| 2019/0318825 A1 | 10/2019 | Shaw | |
| 2019/0340546 A1* | 11/2019 | Goldman-Shenhar | G06Q 10/02 |
| 2020/0100084 A1 | 3/2020 | Martin et al. | |
| 2020/0143938 A1* | 5/2020 | Kakhki | G06Q 10/02 |
| 2020/0210960 A1* | 7/2020 | Soryal | G01C 21/343 |
| 2021/0012261 A1* | 1/2021 | Fukuda | G08G 1/0969 |
| 2021/0150490 A1* | 5/2021 | Koch | G06Q 10/1097 |

OTHER PUBLICATIONS

Gou et al., Information Reminding Method and Device, Mobile Terminal, Chinese Patent Publication No. CN 111432336 B, Aug. 27, 2021 (machine translation) (Year: 2021).*

Zhuofei, Service Processing Method and Device, Korean Publication No. KR 20210035883 A, Sep. 7, 2018 (machine translation) (Year: 2018).*

M. Kocsis, J. Winckler, N. Sußmann and R. Zöllner, "Interactive Mission Planning System of an Autonomous Vehicle Fleet that Executes Services," 2020 IEEE 23rd International Conference on Intelligent Transportation Systems (ITSC), Rhodes, Greece, 2020, pp. 1-6, doi: 10.1109/ITSC45102.2020.9294595. (Year: 2020).*

Gandolf, Stewart; "15 Healthcare Marketing Strategies That Deliver More Healthcare Patients"; (https://healthcaresuccess.com/blog/healthcare-marketing/healthcare-marketing-strategy.html); Oct. 30, 2020; 24 pgs.

International Search Report and Written Opinion for PCT/US2022/022431, dated Jun. 28, 2022, 13 Pages.

* cited by examiner

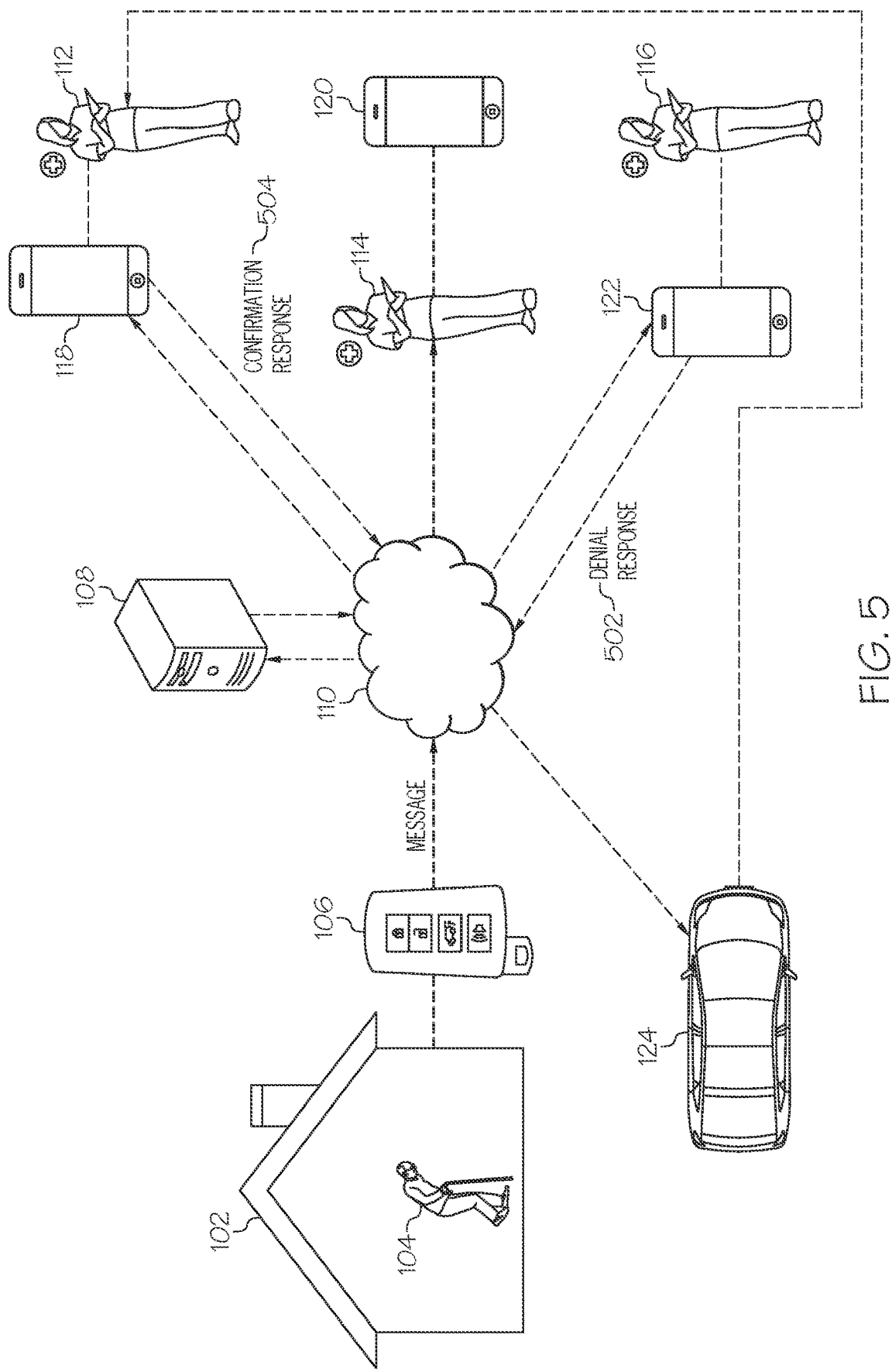

METHODS AND SYSTEMS FOR IDENTIFYING SERVICE PROVIDERS AND PROVIDING SERVICES

TECHNICAL FIELD

The embodiments described herein generally relate to facilitating the provision of services to individuals, and more specifically, to identifying qualified service providers and granting these service providers access to locations associated with individuals seeking services.

BACKGROUND

Conventionally, individuals that are in need of medical services were required to physically travel to hospitals, clinics, and other such facilities. While individuals in need of medical services are able to call an ambulance in times of emergencies, resource and transportation constraints limit ambulance response times. Moreover, ambulances or medical vehicles nearest to the individuals may not be notified, or even if notified, may lack the ability to access the location in which these individuals reside, e.g., due to the incapacity on the part of these individuals. As a result, these individuals may not be provided with critical medical care in time.

Accordingly, a need exists for a system that identifies qualified medical service professionals within a certain proximity of sick individuals and granting these medical service professionals access to locations in which these individuals reside, in addition to transporting these medical service professionals to these locations.

SUMMARY

In one embodiment, a system for facilitating the provision of services to individuals via the communication of digital authorization data is provided. The system includes a processor that is configured to receive a message from a first device of a first user, the message including a request and digital authorization data associated with the first user, identify, within a proximity of a first location of the first device, a second device of a second user capable of performing an action associated with the request, determine whether the second user provided agreement to perform the action, communicate the digital authorization data to the second device of the second user responsive to determining that the second user provided the agreement, and instruct, responsive to determining that the second user provided the agreement, a vehicle to transport the second user from a second location of the second device to the first location.

In another embodiment, a method for facilitating the provision of services to individuals via the communication of digital authorization data is provided. The method includes receiving a message from a first device of a first user, the message including a request and digital authorization data associated with the first user, identifying, within a proximity of a first location of the first device, a second device of a second user capable of performing an action associated with the request, determining whether the second user provided agreement to perform the action, communicating the digital authorization data to the second device of the second user responsive to determining that the second user provided the agreement, and instructing, responsive to determining that the second user provided the agreement, a vehicle to transport the second user from a second location of the second device to the first location.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 5 schematically depicts another example operation of the provider identification system of the present disclosure, according to one or more embodiments described and illustrated herein.

DETAILED DESCRIPTION

The embodiments disclosed herein describe a system and method for identifying qualified service providers and granting these service providers access to various facilities in which individuals are present. As stated above, conventional systems that facilitate the provision of medical assistance to individuals has numerous limitations. Specifically, resource constraints and time constraints (e.g., a large geographic area covered by a limited number of hospitals, ambulances, and medical staff) may limit the speed and effectiveness with which emergency medical services are provided to patients.

To address and overcome these limitations, the provider identification system of the present disclosure is configured to, upon receiving a distress signal from an individual, identify a plurality of suitable and capable medical service providers with a certain proximity of the location of the individual, secure confirmation for the provision of medical services from one or more of these service providers, transmit digital authorization data to one or more devices associated with these service providers, and dispatch the vehicle to transport one or more of these service providers from their respective locations to the location of the individual. The digital authorization data enables the one or more medical services providers to gain access to the location of the individual that transmitted the distress signal, e.g., the home or office of the individual. In this way, the provision of requisite medical services to individuals in need is ensured.

Figure 1:
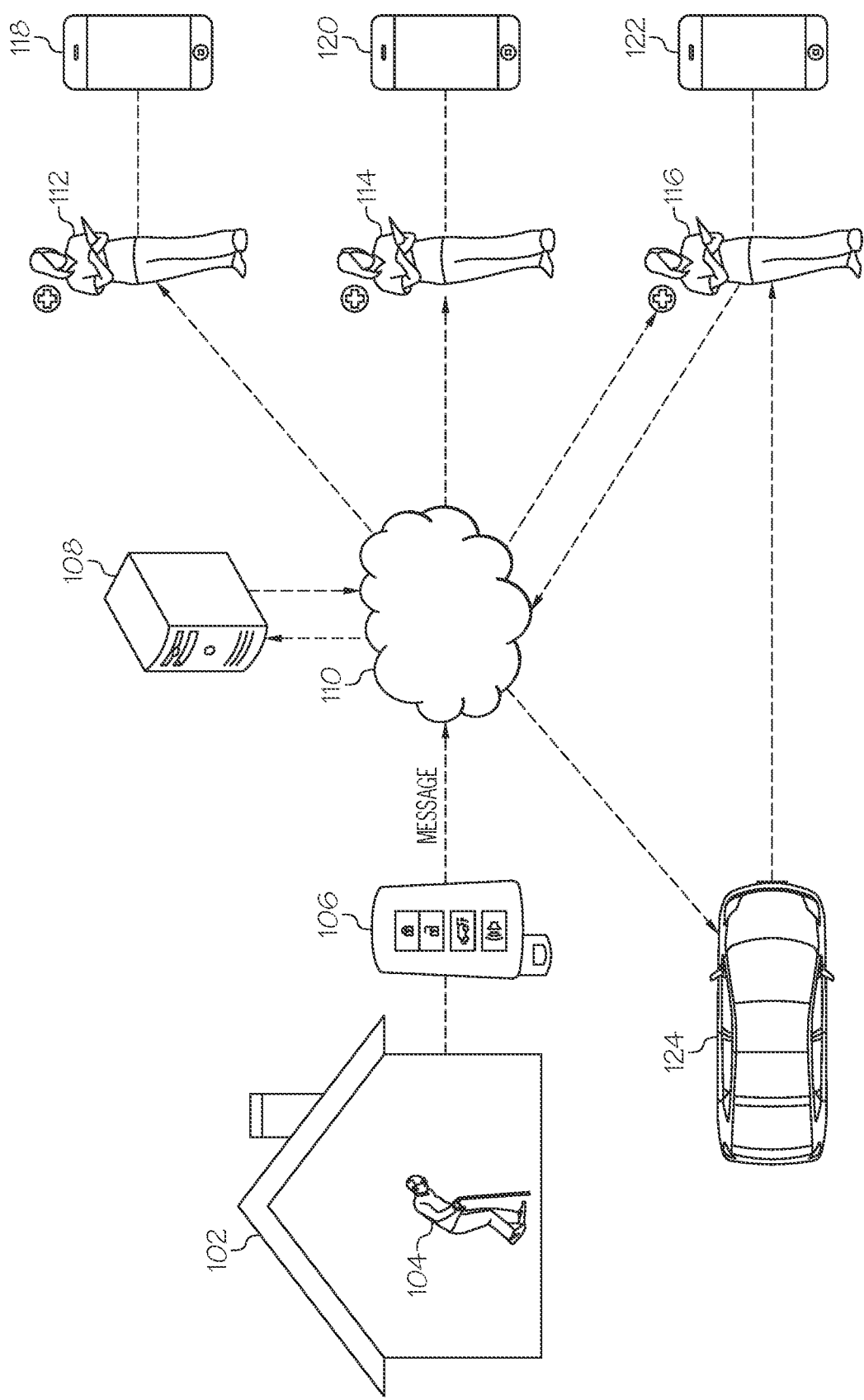
FIG. 1 schematically depicts an example operating environment of the provider identification system of the present disclosure, according to one or more embodiments described and illustrated herein.

FIG. 1 schematically depicts an example operating environment of the provider identification system of the present disclosure, according to one or more embodiments described and illustrated herein. As illustrated, FIG. 1 depicts an individual 104 residing in a house 102. The individual 104 may be an elderly person that experiences a medical ailment, e.g., chest pains, shortness of breath, and so forth. When the individual 104 experiences such an ailment, the individual 104 may interact with a device such as a digital keyfob 106.

In embodiments, the device may also be a smartphone, a laptop, a medical device operating independently, a medical device that is integrated as part of one or more devices, any smart device at home, and so forth. It is noted that all of these devices may operate in a manner that is comparable to the digital keyfob 106. An SOS message, a text message, and/or an audio message may be transmitted by the digital keyfob 106 (or any of these other devices) and received by the server 108 via the communication network 110. The message may include a request for medical services and digital authorization data that provides access to a location (e.g., the house 102) of the individual 104. Alternatively, the message may include a request for other services, e.g., assistance with the purchase of groceries, automotive services, and so forth.

Thereafter, the server 108, which may be a combination of one or more servers, identifies a plurality of users 112, 114, and 116, and devices 118, 120, and 122 that are associated with these users within a certain proximity of the digital keyfob 106, e.g., 2 miles, 3 miles, 5 miles, etc. Each of the users 112, 114, and 116 may be capable of performing one or actions associated with the request for medical services, namely providing adequate medical services to the individual 104. The server 108 may then identify a device of one of these medical service providers as being closest to the house 102, request confirmation or acceptance for the provision of medical services from the medical service provider, and determine whether the confirmation was received. Upon receipt of confirmation, the server 108 may transmit digital authorization data to the device of the selected medical service provider and instruct a designated vehicle 124 to transport this medical service provider to the house 102. The medical service provider may then utilize the digital authorization data to access the house 102 and provide the individual 104 with medical services.

Figure 2:
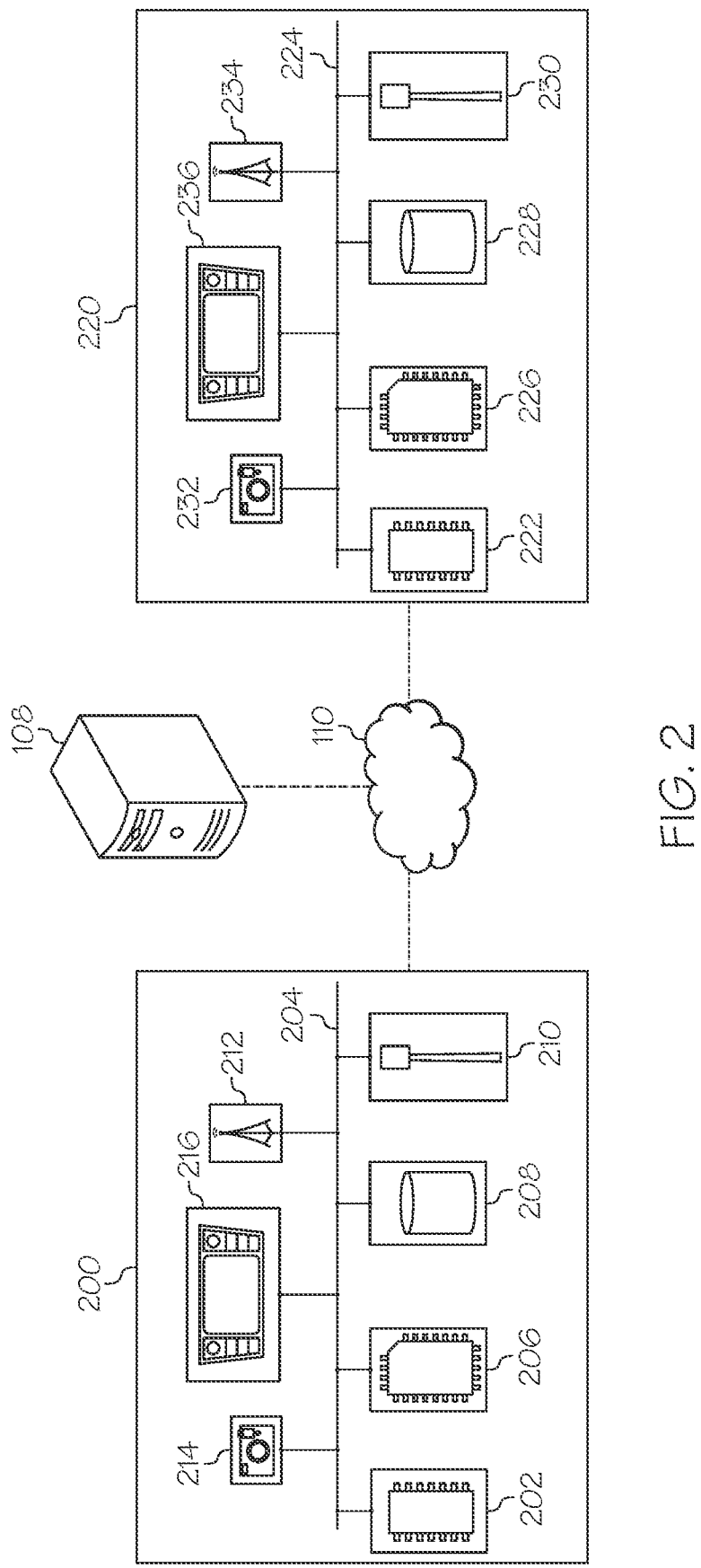
FIG. 2 schematically depicts non-limiting components of the vehicles and the devices of the present disclosure, according to one or more embodiments described and illustrated herein.

FIG. 2 schematically depicts non-limiting components of the devices of the present disclosure, according to one or more embodiments described and illustrated herein.

FIG. 2 schematically depicts non-limiting components of a mobile device system 200 and a vehicle system 220, according to one or more embodiments shown herein. Notably, while the mobile device system 200 is depicted in isolation in FIG. 2, the mobile device system 200 may be included within a vehicle. A vehicle into which the vehicle system 220 may be installed may be an automobile or any other passenger or non-passenger vehicle such as, for example, a terrestrial, aquatic, and/or airborne vehicle. In some embodiments, these vehicles may be autonomous vehicles that navigate their environments with limited human input or without human input.

The mobile device system 200 and the vehicle system 220 may include processors 202, 222. The processors 202, 222 may be any device capable of executing machine readable and executable instructions. Accordingly, the processors 202, 222 may be a controller, an integrated circuit, a microchip, a computer, or any other computing device.

The processors 202, 222 may be coupled to communication paths 204, 224, respectively, that provide signal interconnectivity between various modules of the mobile device system 200 and vehicle system 220. Accordingly, the communication paths 204, 224 may communicatively couple any number of processors (e.g., comparable to the processors 202, 222) with one another, and allow the modules coupled to the communication paths 204, 224 to operate in a distributed computing environment. Specifically, each of the modules may operate as a node that may send and/or receive data. As used herein, the term "communicatively coupled" means that the coupled components are capable of exchanging data signals with one another such as, for example, electrical signals via conductive medium, electromagnetic signals via air, optical signals via optical waveguides, and the like.

Accordingly, the communication paths 204, 224 may be formed from any medium that is capable of transmitting a signal such as, for example, conductive wires, conductive traces, optical waveguides, or the like. In some embodiments, the communication paths 204, 224 may facilitate the transmission of wireless signals, such as WiFi, Bluetooth®, Near Field Communication (NEC) and the like. Moreover, the communication paths 204, 224 may be formed from a combination of mediums capable of transmitting signals. In one embodiment, the communication paths 204, 224 comprises a combination of conductive traces, conductive wires, connectors, and buses that cooperate to permit the transmission of electrical data signals to components such as processors, memories, sensors, input devices, output devices, and communication devices. Accordingly, the communication paths 204, 224 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The mobile device system 200 and the vehicle system 220 include one or more memory modules 206, 226 respectively, which are coupled to the communication paths 204, 224. The one or more memory modules 206, 226 may comprise RAM, ROM, flash memories, hard drives, or any device capable of storing machine readable and executable instructions such that the machine readable and executable instructions can be accessed by the processors 202, 222, The machine readable and executable instructions may comprise logic or algorithm(s) written in any programming language of any generation (e.g., 1GL, 2GL, 3GL, 4GL, or 5GL) such as, for example, machine language that may be directly executed by the processors 202, 222 or assembly language, object-oriented programming (OOP), scripting languages, microcode, etc., that may be compiled or assembled into machine readable and executable instructions and stored on the one or more memory modules 206, 226. Alternatively, the machine readable and executable instructions may be written in a hardware description language (HDL), such as logic implemented via either a field-programmable gate array (FPGA) configuration or an application-specific integrated circuit (ASIC), or their equivalents. Accordingly, the methods described herein may be implemented in any conventional computer programming language, as pre-programmed hardware elements, or as a combination of hardware and software components. In some embodiments, the one or more memory modules 206, 226 may store data related to status and operating condition information related to one or more vehicle components, e.g., brakes, airbags, cruise control, electric power steering, battery condition, and so forth. The memory modules 206, 226 may also store identity data associated with various users, digital authorization data associated with various locations (e.g., residential and commercial properties), vehicles, and devices.

The mobile device system 200 and the vehicle system 220 may include one or more sensors 208, 228. Each of the one or more sensors 208, 228 is coupled to the communication paths 204, 224 and communicatively coupled to the processors 202, 222. The one or more sensors 208 may include one or more motion sensors for detecting and measuring motion and changes in motion of the vehicle. The motion sensors may include inertial measurement units. Each of the one or more motion sensors may include one or more accelerometers and one or more gyroscopes. Each of the one or more motion sensors transforms sensed physical movement of the vehicle into a signal indicative of an orientation, a rotation, a velocity, or an acceleration of the vehicle. The one or more sensors may also include a microphone, a motion sensor, a proximity sensor, and so forth. The sensors 208, 228 may be able to detect the proximity of one or more devices and initiate the transmission to data (e.g., digital authorization data) upon detecting these devices (e.g., smartphones of various users) within a certain proximity from these sensors.

Still referring, to FIG. 2, the mobile device system 200 and the vehicle system 220 optionally includes satellite antennas 210, 230 coupled to the communication paths 204, 224 such that the communication paths 204, 224 communicatively couple the satellite antennas 210, 230 to other modules of the mobile device system 200. The satellite antennas 210, 230 are configured to receive signals from global positioning system satellites. Specifically, in one embodiment, the satellite antennas 210, 230 include one or more conductive elements that interact with electromagnetic signals transmitted by global positioning system satellites. The received signal is transformed into a data signal indicative of the location (e.g., latitude and longitude) of the satellite antennas 210, 230 or an object positioned near the satellite antennas 210, 230, by the processors 202, 222. The location information may be include the data regarding the location of the plurality of the users 112, 114, 116, the designated vehicle 124, and other external devices.

The mobile device system 200 and the vehicle system 220 may include network interface hardware 212, 234 for communicatively coupling the mobile device system 200 and the vehicle system 220 with the server 108, e.g., via communication network 110. The network interface hardware 212, 234 is coupled to the communication paths 204, 224 such that the communication path 204 communicatively couples the network interface hardware 212, 234 to other modules of the mobile device system 200 and the vehicle system 220. The network interface hardware 212, 234 may be any device capable of transmitting and/or receiving data via a wireless network, e.g., the communication network 110. Accordingly, the network interface hardware 212, 234 may include a communication transceiver for sending and/or receiving data according to any wireless communication standard. For example, the network interface hardware 212, 234 may include a chipset (e.g., antenna, processors, machine readable instructions, etc.) to communicate over wireless computer networks such as, for example, wireless fidelity (Wi-Fi), WiMax, Bluetooth®, IrDA, Wireless USB, Z-Wave, ZigBee, or the like. In some embodiments, the network interface hardware 212, 234 includes a Bluetooth® transceiver that enables the mobile device system 200 and the vehicle system 220 to exchange information with the server 108 via Bluetooth®.

The network interface hardware 212, 234 may utilize various communication protocols to establish a connection between multiple mobile device and/or vehicles. For example, in embodiments, the network interface hardware 212, 234 may utilize a communication protocol that enables communication between a vehicle and various other devices, e.g., vehicle-to-everything (V2X). Additionally, in other embodiments, the network interface hardware 212, 234 may utilize a communication protocol that is dedicated for short range communications (DSRC). Compatibility with other comparable communication protocols are also contemplated.

It is noted that communication protocols include multiple layers as defined by the Open Systems Interconnection Model (OSI model), which defines a telecommunication protocol as having multiple layers, e.g., Application layer, Presentation layer, Session layer, Transport layer, Network layer, Data link layer, and Physical layer. To function correctly, each communication protocol includes a top layer protocol and one or more bottom layer protocols. Examples of top layer protocols (e.g., application layer protocols) include HTTP, HTTP2 (SPDY), and HTTP3 (QUIC), which are appropriate for transmitting and exchanging data in general formats. Application layer protocols such as RTP and RTCP may be appropriate for various real time communications such as, e.g., telephony and messaging. Additionally, SSH and SFTP may be appropriate for secure maintenance, MQTT and AMQP may be appropriate for status notification and wakeup trigger, and MPEG-DASH/HLS may be appropriate for live video streaming with user-end systems. Examples of transport layer protocols that are selected by the various application layer protocols listed above include, e.g., TCP, QUIC/SPDY, SCTP, DCCP, UDP, and RUDP.

The mobile device system 200 and the vehicle system 220 include cameras 214, 232. The cameras 214, 232 may have any resolution. In some embodiments, one or more optical components, such as a mirror, fish-eye lens, or any other type of lens may be optically coupled to the cameras 214, 232. In embodiments, the camera may have a broad angle feature that enables capturing digital content within a 150 degree to 180 degree arc range. Alternatively, the cameras 214, 232 may have a narrow angle feature that enables capturing digital content within a narrow arc range, e.g., 60 degree to 90 degree arc range. In embodiments, the one or more cameras may be capable of capturing high definition images in a 720 pixel resolution, a 1080 pixel resolution, and so forth. The cameras 214, 232 may capture images of a face or a body of users 112, 114, 116 and facilitate the performance of one or more identity authentication operations by the server 108.

In embodiments, the mobile device system 200 and the vehicle system 220 may include displays 216, 236 for providing visual output. The displays 216, 236 may output digital data, images and/or a live video stream of various types of data. The displays 216, 236 are coupled to the communication paths 204, 224. Accordingly, the communication paths 204, 224 communicatively couple the displays 216, 236 to other modules of the mobile device system 200 and the vehicle system 220, including, without limitation, the processors 202, 222 and/or the one or more memory modules 206, 226. The displays 216, 236 may be configured to display digital authorization data, distress messages, and so forth.

Still referring to FIG. 2, the server 108 may be a cloud server with one or more processors, memory modules, network interface hardware, and a communication path that communicatively couples each of these components. It is noted that the server 108 may be a single server or a combination of servers communicatively coupled together.

Figure 3:
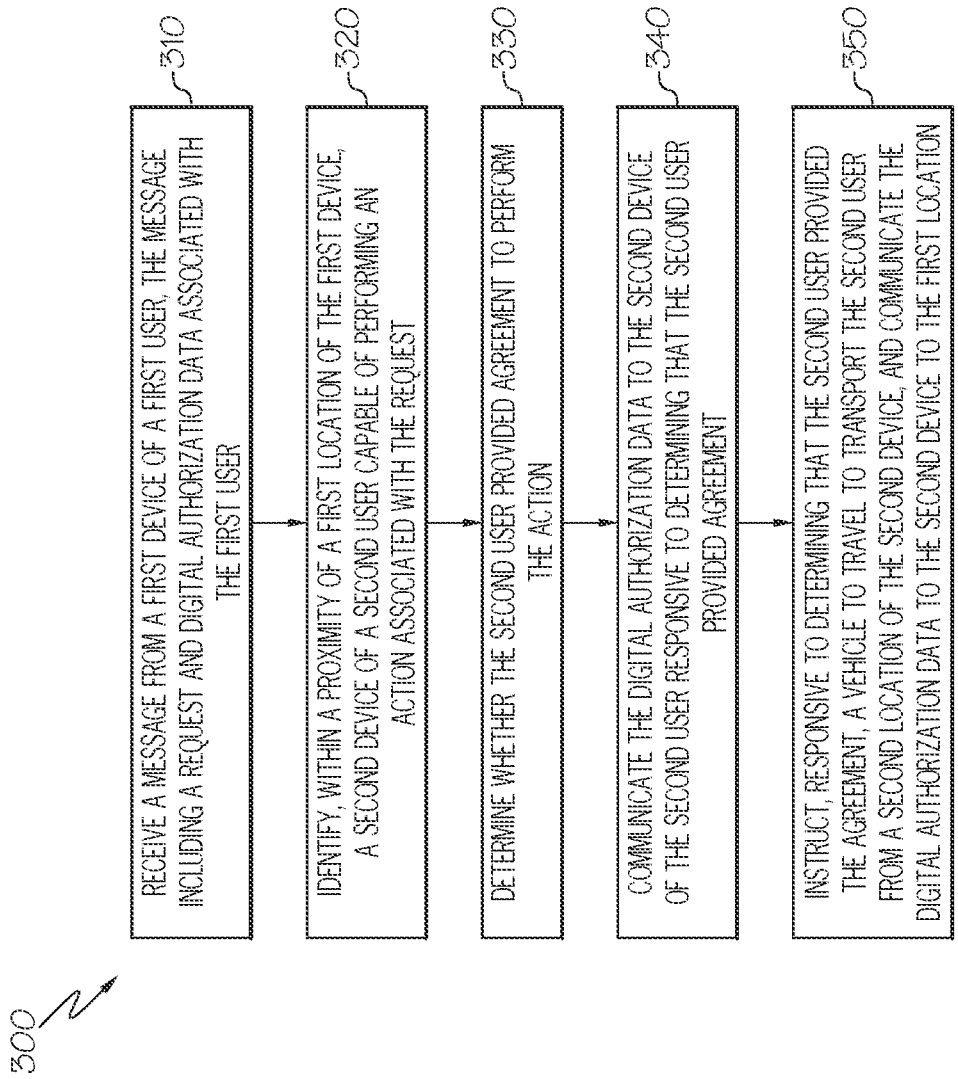
FIG. 3 depicts a flow chart for facilitating the provision of services to individuals, according to one or more embodiments described and illustrated herein.

FIG. 3 depicts a flow chart for facilitating the provision of medical services to individuals, according to one or more embodiments described and illustrated herein. In block 310, the server 108 may receive a message from a device associated with a user (e.g., a first device such as the digital keyfob 106 that is associated the individual 104 as described in FIG. 1). The message may include a request (e.g., for the provision of medical services) and digital authorization data associated with a location of the user. In embodiments, the message may be a question, a distress signal, or the like, indicating that the individual 104 is suffering and is in need of medical assistance. Alternatively, the message may be a question, a distress signal, or the like, associated with the need for other services, e.g., assistance with automotive services, the purchase for basic necessities like groceries, and so forth.

In embodiments, the digital authorization data may provide access to the home of individual 104. For example, the digital authorization data may be, e.g., an RFID code or barcode that enables medical service personnel to access a home of the individual 104. Such a code may be accessible via a software application of a smartphone, and an owner of the smartphone may bring the barcode displayed on smartphone within a certain proximity of another device that is located external to the house 102 of the individual 104 (e.g., near the front door) and gain access to the house 102. It is noted that the digital authorization data may also enable access to a vehicle of the individual 104, or other devices associated with the individual 104.

In block 320, the server 108 may identify, within a proximity of a first location of the first device, a second device of a second user capable of performing an action associated with the request. For example, if the request relates to the need for medical services, the server 108 may identify a plurality of medical services providers, each of whom may be capable of providing the medical services to the individual 104. In particular, the server 108 may identify the presence of the devices associated each of these medical service providers. These service providers may all be located within a certain proximity of the device from which the request was received, e.g., within a 5 mile radius of the example house 102 of the individual 104. In embodiments, the server 108 may store the contact information associated with these medical service providers (e.g., names, phone numbers, email addresses, and so forth), information associated with smartphones, laptops, etc., associated with these medical service providers, and so forth. This data may be stored locally in memory of the server 108, or may be accessed from memory of third party servers, various external devices, or vehicles systems with which the server 108 communicates, e.g., via the communication network 110.

After identifying a plurality of medical services providers, the server 108 may identify a particular device associated with a medical service provider (e.g., a second device) that is closest to the first device (e.g., the digital keyfob 106) and transmit a message specifically to this device. In embodiments, the message may be a text message that is output onto a display of the device indicating the distress signal received from the individual 104. For example, the message may state "Emergency—elderly patient is suffering from chest pains—Travel to patient's home immediately". Additionally, the message may include a request for agreement from the medical service provider. For example, the message may state "Do you agree to provide the medical services". In response, the medical service provider that is closest to the first device and closest to the example house 102 may transmit his agreement to provide the medical services. In return, the medical service provider may receive payment upon provision of the services.

In block 330, the server 108 may determine whether the second user (e.g., the medical service provider that is closest to the digital keyfob 106 of the individual 104) provided agreement to perform the action. In embodiments, this step may include the server 108 performing an authentication operation upon receiving an agreement or confirmation message from the device of the medical service provider. The authentication operation may include, e.g., checking and confirming the name, address, device identification information of the medical service provider, and so forth. As stated, such data may be stored locally in memory of the server 108 or may be accessible from the memory of third party servers, various external devices, or vehicles systems with which the server 108 communicates, e.g., via the communication network 110.

In block 340, upon confirming that confirmation was received from the second user, the server 108 may communicate the digital authorization data to the device associated with the second user (e.g., smartphone, laptop, and so forth). As stated, the digital authorization data may enable the medical service provider to access a location in which the individual 104 may be residing.

In block 350, the server 108 may instruct, responsive to determining that the second user provided the agreement, a vehicle to transport the second user from a second location of the second device to the first location. For example, after confirming that a particular medical services provider has given his agreement to provide the medical services, the designated vehicle may serve to transport the medical services provider from his current location to the location where the medical services need to be provided, e.g., the house 102. In this way, even if the medical services provider does not have available transportation facilities, he or she may be able to Reach the location of a person in need of medical services.

Figure 4:
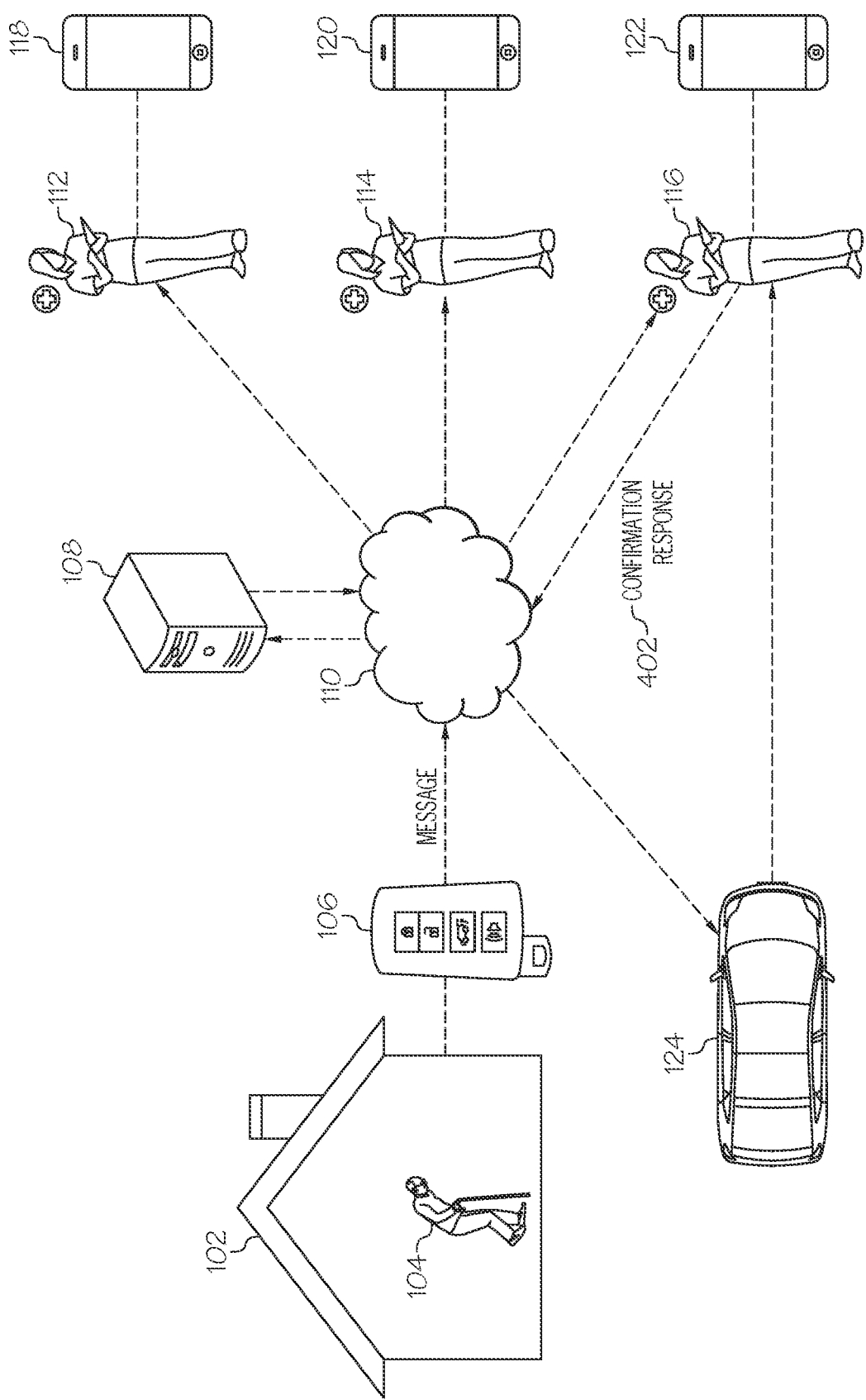
FIG. 4 schematically depicts an example operation of the provider identification system of the present disclosure, according to one or more embodiments described and illustrated herein.

FIG. 4 schematically depicts an example operation of the provider identification system of the present disclosure, according to one or more embodiments described and illustrated herein.

As illustrated in FIG. 4, the individual 104 may be an elderly person living alone, and as such, may not have access to or may be unable to travel to a hospital or medical facility without assistance. Such a person may be particularly susceptible to further injury if he or she is not provided with prompt and adequate medical assistance. The individual 104, depicted in FIG. 4, may press a button on the digital keyfob 106, which may initiate a message in the form of a distress signal to the server 108. In embodiments, the message may be a text message indicating that the individual is in urgent need for medical assistance. The message may also include digital authorization data that enables a medical services provider to access a location in which the individual 104 may be staying, e.g., the house 102. In other embodiments, the individual 104 may have the ability to transmit a message requesting the provision of automotive services, assistance with the purchase of groceries, and so forth.

In response to receiving the message, the server 108 may identify a plurality of users 112, 114, 116 and their respective devices 118, 120, 122, each of whom may be able to perform one or more actions associated with the request. These users may be medical services providers. Additionally, if the request was related to the need for automotive services or for the purchase of necessities (e.g., groceries), the users that are identified may be automotive service providers, temporary assistants, and so forth, After identifying the users 112, 114, 116 and their respective devices 118, 120, 122, the server 108 may select a user (and his associated device) that is closest to the location of the distress signal, e.g., the house 102 of the individual 104. The server 108 may also transmit a message inquiring whether the selected user, e.g., the user 116 as illustrated in FIG. 4, is willing to provide the medical services. The user 116 may be a medical service provider that is closest to the location of the individual 104, e.g., within 3 miles, while users 112, 114 and their respective devices 118 and 120 may be 4 miles and 5 miles away from the individual 104.

In embodiments, a message from the server 108 may appear on the display of a smartphone of the medical service provider. In response, the user 116 may transmit a confirmation response 402 (e.g., a reply message) indicating his intent and willingness to travel to the location of the individual 104 and provide the requisite medical services. In embodiments, the confirmation response 402 may be a selection of a simple "Yes", or "No" that may appear on the display of the device 122 (e.g., a smartphone). It is noted that such a message may also be output onto other devices, e.g., laptop, desktop, in-vehicle display, and so forth. In embodiments, the server 108, upon receiving the confirmation response 402, may perform an authentication operation to confirm the identity of the user 116 and the device 122. Upon authenticating the identity of the user 116, the server 108 may communicate digital authorization data to the device 122 of the user 116, which will enable the user to gain access to the house 102 of the individual 104 and provide the requisite medical services. Additionally, after transmission of the digital authorization data, the server 108 may instruct the designated vehicle 124 to transport the user 116 from his location to the location of the individual 104. In this way, response times associated with emergency medical assistance requests are improved.

In other embodiments, the server 108 may transmit the message the distress signal) received from the keyfob 106 to each of the devices 118, 120, 122 of the plurality of users 112, 114, 116, and may receive confirmation responses from each of these users. In other words, multiple users, each of whom are capable of providing medical services may transmit their intent and willingness to provide medical services. In response, the server 108 may access preference criteria provided by the individual 104. The preference criteria may be stored locally in the digital keyfob 106 (or a smartphone, laptop, and so forth associated with the individual 104) or may be accessible in a database associated with the server 108 that is external to any devices of the individual 104. Based on this preference criteria, the server 108 may, automatically and without user intervention, select at least one of the plurality of users 112, 114, 116.

In embodiments, the preference criteria may be based on skill level, experience level, cost of performing a particular action, and distance to the location of the individual 104 (e.g., a first location). As such, the server 108 may select a user from the plurality of users 112, 114, 116 that has the most experience providing medical services. In other embodiments, a user that has an exceptionally high rating, high skill level, or one that has previously provided medical services to the individual 104 may be selected. Other examples of preference criteria are also contemplated.

FIG. 5 schematically depicts another example operation of the provider identification system of the present disclosure, according to one or more embodiments described and illustrated herein.

It is noted that the example operation illustrated in FIG. 5 is similar to the example operation described in FIG. 4. However, in the example operation illustrated in FIG. 5, the user 116 may receive a message from server 108, inquiring whether the selected user, e.g., the user 116 illustrated in FIG. 4, and respond by indicating his unwillingness to provide the medical services. Specifically, the user 116 may transmit a denial response 502 (e.g., denial message) to the server 108. Upon receiving the denial response 502, the server 108 may, automatically and without user intervention, identify another user based on a proximity relative to the individual 104 and the digital keyfob 106. For example, the server 108 may identify the device 118 of the user 112, who may be a medical service provider who is located 4 miles away (e.g., an additional location at a different proximity relative to the house 102) from the individual 104 (as opposed to the user 116 who may be 3 miles away). The user 112 may transit a confirmation response 504 indicating his intent and willingness to travel to the location of the individual 104 and provide the requisite medical services. It is noted that if the user 112 also transmits a denial response, the server 108 may identify the device 120 (e.g., a third device) of the user 114 (e.g., a third user), determine whether the third user provided agreement, and so forth.

In embodiments, the server 108 may receive the confirmation response 504, authenticate the identity of the user 112, and transmit the digital authorization data associated with the location of the individual 104 to the designated vehicle 124. The designated vehicle 124 may then travel to the location of the user 112, transmit the digital authorization data to the device 118 associated with the user 112, in addition to transporting the user 112 to the location of the individual 104, e.g., the house 102. Even if a particular medical service provider is unable to provide adequate medical services, the service provider system of the present disclosure may, automatically and without user intervention, identify another service provider within an identical or similar proximity. In this way, the provision of critical medical services for individuals may be ensured.

It should be understood that the embodiments described herein relate to a method for generating and outputting composite images on displays of vehicles. The method includes receiving a signal from a device that is external to the vehicle, the signal including identification data of an object associated with the device, comparing the identification data with the user identifications stored in the memory of the vehicle, and granting, to the object, access to the first set of functionalities of the vehicle in response to determining that the identification data matches the first user identification.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A system comprising:
   a processor configured to:
     receive a message from a first device of a first user, the message including a request and digital authorization data associated with the first user;
     identify, within a proximity of a first location of the first device, a second device of a second user capable of performing an action associated with the request;
     determine whether the second user provided agreement to perform the action; communicate the digital authorization data to the second device of the second user responsive to determining that the second user provided agreement; and
     instruct, responsive to determining that the second user provided the agreement, a vehicle to transport the second user from a second location of the second device to the first location; and the vehicle configured to autonomously navigate from the second location to the first location in response to receiving the instruction from the processor, wherein the digital authorization data includes a code and provides access to a home of the first user and the vehicle, the second device is a mobile device configured to display the code, and the code provides access to the home when the code is displayed on the second device and is brought within a certain proximity of another device that is located external to the home.

2. The system of claim 1, wherein the processor determining whether the second user provided agreement to perform the action includes:

receiving a replay message from the second device; and analyzing the reply message to determine whether the reply message is a confirmation message.

3. The system of claim 1, wherein the processor is further configured to:

identify, within a different proximity of the first location of the first device, responsive to receiving a denial message from the second device, a third device of a third user capable of performing the action associated with the request;

determine whether the third user has provided agreement to perform the action;

communicate the digital authorization data to the third device responsive to determining that the third user provided the agreement; and instruct, responsive to determining that the third user provided the agreement, the vehicle to autonomously navigate from a third location to the first location to transport the third user from the third location of the third device to the first location.

4. The system of claim 3, wherein the processor determining whether the third user provided agreement to perform the action includes:

receiving a reply message from the third device in response to the request; and analyzing the reply message to determine whether the reply message is a confirmation message.

5. The system of claim 1, wherein the processor is further configured to:

identify, within a different proximity of the first location of the first device, a third device of a third user capable of performing the action associated with the request;

determine whether the third user has provided agreement to perform the action; and select automatically, based on preference criteria, at least one of the second user and the third user for performing the action.

6. The system of claim 5, wherein the preference criteria is based on at least one of skill level, experience level, cost of performing the action, and a distance to the first location.

7. The system of claim 1, wherein the request is related to medical assistance or automotive services.

8. The system of claim 1, wherein the vehicle is an autonomous vehicle.

9. The system of claim 1, wherein the processor is configured to instruct, responsive to determining that the second user provided the agreement, the vehicle to autonomously navigate to the second location.

10. The system of claim 1, wherein the digital authorization data provides access to a vehicle of the first user.

11. A method comprising:

receiving a message from a first device of a first user, the message including a request and digital authorization data associated with the first user;

identifying, within a proximity of a first location of the first device, a second device of a second user capable of performing an action associated with the request;

determining whether the second user provided agreement to perform the action; communicating the digital authorization data to the second device of the second user responsive to determining that the second user provided the agreement;

instructing, responsive to determining that the second user provided the agreement, a vehicle to transport the second user from a second location of the second device to the first location; and operating the vehicle to autonomously navigate from the second location to the first location in response to the instruction, wherein the digital authorization data includes a code and provides access to a home of the first user and the vehicle, the second device is a mobile device configured to display the code, and the code provides access to the home when the code is displayed on the second device and is brought within a certain proximity of another device that is located external to the home.

12. The method of claim 11, wherein determining whether the second user provided agreement to perform the action includes:

receiving a reply message from the second device; and analyzing the reply message to determine whether the reply message is a confirmation message.

13. The method of claim 11, further comprising:

identifying, within a different proximity of the first location of the first device, responsive to receiving a denial message from the second device, a third device of a third user capable of performing the action associated with the request;

determining whether the third user has provided agreement to perform the action;

communicating the digital authorization data to the third device responsive to determining that the third user provided the agreement; and instructing, responsive to determining that the third user provided the agreement, the vehicle to autonomously navigate from a third location to the first location to transport the third user from the third location of the third device to the first location.

14. The method of claim 11, wherein the request is related to medical assistance or automotive.

* * * * *

UNITED STATES PATENT AND TRADEMARK OFFICE
CERTIFICATE OF CORRECTION

| | |
|---|---|
| PATENT NO. | : 11,657,343 B2 |
| APPLICATION NO. | : 17/218499 |
| DATED | : May 23, 2023 |
| INVENTOR(S) | : Masashi Nakagawa |

It is certified that error appears in the above-identified patent and that said Letters Patent is hereby corrected as shown below:

In the Specification

In Column 4, Line(s) 12, delete "NEC" and insert --NFC--, therefore.

In Column 5, Line(s) 29, before "include", delete "be".

In Column 5, Line(s) 61, after "mobile", delete "device" and insert --devices--, therefore.

In Column 6, Line(s) 67, after "associated", insert --with--.

Signed and Sealed this
Fourth Day of July, 2023

Katherine Kelly Vidal
*Director of the United States Patent and Trademark Office*